(12) United States Patent
Eda et al.

(10) Patent No.: US 7,231,240 B2
(45) Date of Patent: Jun. 12, 2007

(54) PSYCHOLOGICAL STATE ASSESSMENT DEVICE, PSYCHOLOGICAL STATE ASSESSMENT METHOD

(75) Inventors: Hideo Eda, Tokyo (JP); Yasufumi Kuroda, Tokyo (JP); Takanori Maesako, Osaka (JP); Katsuo Sugai, Osaka (JP)

(73) Assignee: National Institute of Information and Communications Technology, Tokyo (JP)

( * ) Notice: Subject to any disclaimer, the term of this patent is extended or adjusted under 35 U.S.C. 154(b) by 261 days.

(21) Appl. No.: 11/034,366

(22) Filed: Jan. 11, 2005

(65) Prior Publication Data
US 2005/0154322 A1 Jul. 14, 2005

(30) Foreign Application Priority Data
Jan. 14, 2004 (JP) ............................ P2004-007365

(51) Int. Cl.
*A61B 5/00* (2006.01)
(52) U.S. Cl. ...................................... 600/322; 600/323
(58) Field of Classification Search ................ 600/309, 600/310, 322, 323, 326, 328
See application file for complete search history.

(56) References Cited

U.S. PATENT DOCUMENTS

| | | | |
|---|---|---|---|
| 4,694,833 A | 9/1987 | Hamaguri | |
| 4,942,877 A | 7/1990 | Sakai et al. | |
| 5,995,857 A * | 11/1999 | Toomim et al. | 600/322 |
| 6,549,795 B1 | 4/2003 | Chance | |
| 6,829,496 B2 | 12/2004 | Nagai et al. | |
| 7,142,902 B2 | 11/2006 | Eda et al. | |
| 2002/0103428 A1* | 8/2002 | deCharms | 600/410 |
| 2003/0220550 A1* | 11/2003 | McCulloch et al. | 600/323 |
| 2005/0171435 A1 | 8/2005 | Eda et al. | |

FOREIGN PATENT DOCUMENTS

| | | |
|---|---|---|
| EP | 1 447 049 | 8/2004 |
| JP | 06-014908 | 1/1994 |
| JP | 2002-172106 | 6/2002 |
| JP | 2004-170958 | 6/2004 |

OTHER PUBLICATIONS

Sackler Institute; Preliminary Synthesis of the First High Level Forum on Learning Sciences and Brain Research: Potential Implications for Education Policies and Practices: Brain Mechanisms and Early Learning; New York City, NY, USA, Jun. 16-17, 2000, pp. 1-28.

* cited by examiner

*Primary Examiner*—Eric F. Winakur

(57) ABSTRACT

In order to offer a new and useful device in being able to objectively assess the psychological state when a subject performs an assignment, a psychological state assessment device is configured to irradiate a specified measurement site in the brain of a subject with near infrared light of a specified wavelength, to obtain time change data indicating time change data for the amount of blood and/or amount of blood components respectively while performing a task and while at rest, and to assess the psychological state of the subject while performing the assignment based on time change data during the rest period in comparison with time change data while performing the task.

16 Claims, 12 Drawing Sheets

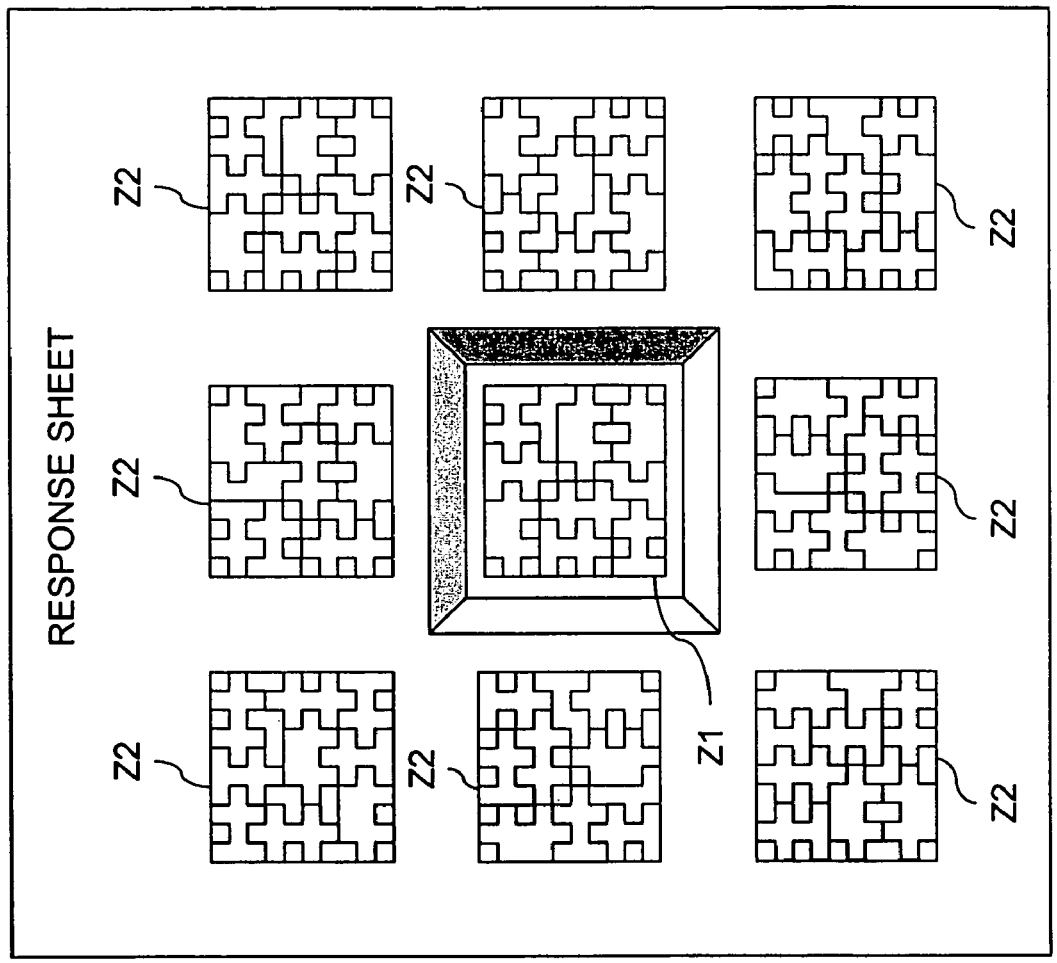
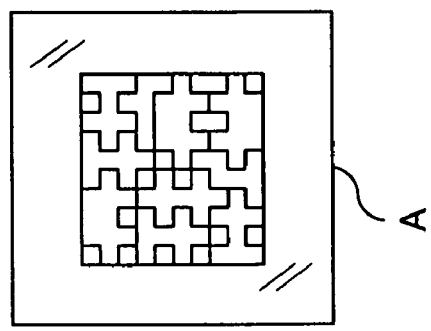
Fig.4

PSYCHOLOGICAL STATE ASSESSMENT DEVICE, PSYCHOLOGICAL STATE ASSESSMENT METHOD

FIELD OF THE INVENTION

The present invention relates to a psychological state assessment device and a psychological state assessment method that, based on scientific data, assess the psychological state of a subject when performing an assignment that comprises multiple tasks and that sets up a rest, a time during which a task is not given, between a specified task and the following task.

DESCRIPTION OF RELATED ART

Recently, a variety of devices have been developed to obtain scientific data indicating brain activity when some kind of assignment is given such as a learning assignment, exercise, or stimulus. Of these, the acquisition of scientific data on brain activity when a subject is made to perform an assignment without being in a severely limited experimental environment has been realized and applied to a variety of fields by developing a device that uses light, specifically, near infrared light, to measure body activity such as brain activity without restricting the subject (refer to Japanese Unexamined Patent Application Publication No. 2004-170958).

In one of these kinds of studies, the subject is made to perform an assignment that comprises multiple tasks and that sets up a rest between a specified task and the following task, a time during which a task is not given, and the brain activity during that interval is measured by observing the time changes of the amount of blood and/or the amount of blood components at, for example, a specified measurement site in the brain.

Often when conducting this kind of brain activity measurement, the amount of blood that temporarily increases when performing the task returns to the normal state (amount of blood and/or the amount of blood components while at rest) during the rest periods when a task is not given, and therefore, the amount of blood and/or the amount of blood components when resting was considered the baseline (background), the measured value when performing the task was then corrected, and the result was taken to be the amount of blood and/or the amount of blood components when performing the task. However, there was no discussion at all about the handling of errors regarding the amount of blood and/or the amount of blood components measured when resting.

SUMMARY OF THE INVENTION

Nonetheless, the present inventors focused on the fact that the amount of blood and/or the amount of blood components may increase rather than decrease when resting if the task given to the subject is highly difficult, and that the subject can have extremely tense feelings prior to performing the task, specifically, while resting.

Then, as a result of repeated assiduous studies, the present inventors discovered, for example: that if a highly stressful task is given to the subject, the amount of blood and/or the amount of blood components while performing the task may not increase because of concentration, and may increase while resting as a form of compensation for this; that the amount of blood may increase while at rest because, unconsciously, motivation becomes heightened for the task to be performed next; and that there is a correlation between the psychological state when performing an assignment and the course of changes over time for the amount of blood and/or the amount of blood components while at rest that was not emphasized in the past.

Thus, a new and useful device not available in the past is offered so that the changes over time in the amount of blood and/or the amount of blood components of a specified measurement site in the brain while at rest can be extracted, and the psychological state during performance of an assignment can be objectively assessed based thereon.

The present invention resolves the aforementioned problems, and is a psychological state assessment device that assesses the psychological state when a subject performs an assignment that comprises multiple tasks and that sets up a rest period as a time during which a task is not given, between a specified task and the following task, comprising: a measurement unit that detects specified parameter signals having a correlation to the amount of blood and/or the amount of blood components in a specified measurement site in the brain of the aforementioned subject, and measures the intensity thereof; a calculator that calculates the amount of blood and/or amount of blood components based on the parameter signal intensities measured by the measurement unit; a time change data generator that generates time change data indicating the time changes of the amount of blood and/or the amount of blood components when a task is being performed and while at rest respectively by acquiring sequentially over time the amount of the blood and/or the amount of the blood components that the calculator calculates; and an output unit that outputs such that a distinction can be made between time change data while performing a task and time change data while resting, both of them are generated by the time change data generator, and also outputs such that the time change data during a specified rest can be compared with time change data while performing the immediately prior and immediately following tasks; and configured such that the psychological state when the subject performs the assignment is assessed based on the aforementioned rest period time change data.

Here "task" means giving any kind of load, work or stimulus to induce bodily activity at a specified site in the body of the subject, and academic tests requiring cognitive capacity, psychological tests, and exercise, as well as other stimuli to the five senses such as vision and olfactory may be cited as examples. In addition to tasks that are completely the same, and similar tasks that are resolved by proceeding with the same means or using the same strategies, "multiple tasks" may also mean different types of tasks. Moreover, there may be one or more "rests".

In addition, in order to be able to make a more accurate assessment, it is preferable to derive individually the baseline corrected amount of blood and/or amount of blood components not only while performing a task, but also while at rest, and it is preferable to make an assessment based on time change data generated in this way; specifically, the calculator may be configured to calculate the baseline corrected amount of blood and/or the amount of blood components when performing the tasks based on the parameter signal intensities measured while performing the task, and to calculate the baseline corrected amount of blood and/or amount of blood components when resting based on the parameter signal intensities measured while at rest.

A concrete aspect of this kind of calculator is such that it calculates as the baseline corrected amount of blood and/or amount of blood components the amount of blood and/or the amount of blood components when the baseline is subtracted from the calculated value of the amount of blood and/or the amount of blood components calculated by specified computations based on the parameter signal intensity, and such that it takes as the baseline the value of the amount of blood and/or the amount of blood components at the initial time when performing the task in relation to the calculated value of the amount of blood and/or the amount of blood components when performing the task.

The calculator further takes as the baseline the value of the amount of blood and/or the amount of blood components at the initial time when resting in relation to the calculated value of the amount of blood and/or the amount of blood components during resting.

This kind of device can set the amount of blood and/or the amount of blood components at the initial time to 0 respectively during a specified performance of a task and during a specified rest period, and can demonstrate what kind of time changes in the amount of blood and/or the amount of blood components occur only while at rest.

Further, it calculates as the baseline corrected amount of blood and/or amount of blood components the amount of blood and/or the amount of blood components when the baseline is subtracted from the calculated value of the amount of blood and/or the amount of blood components calculated by specified computations based on the parameter signal intensity and it is not limited to devices that calculate the baseline corrected amount of blood and/or amount of blood components in the order of first calculating the calculated value of the amount of blood and/or the amount of blood components, and then subtracting the value equivalent to the baseline. As long as the same value is derived, it can include devices that, after conducting baseline correction of parameter signals measured by the measurement unit or of specified intermediary variables derived from the parameter signals, calculate the baseline corrected amount of blood and/or amount of blood components using those corrected parameter signal intensities or intermediary variables. Specifically, for example, baseline correction may be conducted on light absorbance, which is a specified medium variable derived from the intensity of the exiting light equivalent to the parameter signal intensity, and the baseline corrected amount of blood and/or amount of blood components may be calculated utilizing the baseline corrected light absorbance.

In addition, it is preferable that the device of the present invention utilizes near infrared spectroscopy. This is because near infrared light pass through skin tissue and bone tissue to reach the brain. In this case, the device may be configured so that: the measurement unit irradiates the specified measurement site of the brain with near infrared light of a specified wavelength and, based on the irradiated light, measures the intensity of the exiting light comprising the aforementioned parameter signals that exits from the aforementioned measurement site; and the calculator calculates the amount of blood and/or the amount of blood components based on the aforementioned intensity of the exiting light.

Further, utilizing the near infrared spectroscopy of the invention, the device may be configured such that the measurement unit irradiates a specified measurement site of the brain with near infrared light of a specified wavelength, and measures the intensity of the exiting light comprising the aforementioned parameter signals that exit from the aforementioned measurement site based on the irradiated light. The calculator can include a light absorbance time change data generator that calculates the light absorbance of a measurement site at a specified wavelength from the intensity of the exiting light measured by the measurement unit, and generates light absorbance time change data indicating the time changes of the light absorbance; a light absorbance time change data correction unit that conducts baseline corrections of the light absorbance time change data that the light absorbance time change data generator generates respectively while performing a task and while at rest; and a blood amount and/or a blood components amount calculator that calculates the amount of blood and/or the amount of blood components from the light absorbance time change data corrected by the light absorbance time change data correction unit wherein the calculator calculates the baseline corrected amount of blood and/or amount of blood components. Then, the measurement unit that applies near infrared spectroscopy does not require multiple channels, and can realize the full effect of the present invention with a one-channel device.

The amount of blood and/or the amount of blood components that the calculator calculates may be the amount of oxygenated hemoglobin (oxyHb) and amount of deoxygenated hemoglobin (deoxyHb) in the blood of the specified measurement site of the brain. This is because the research of the inventors has revealed that individual differences may be observed in the state of these changes over time, and the psychological state of each subject can be easily grasped thereby.

Moreover, the output unit preferably outputs waveforms of the time change data while the subject is performing a task and also while at rest. This is because the configuration is simple, and the time changes of the amount of blood and/or the amount of blood components when the user performs tasks is immediately and clearly understood.

In brief, this may be a psychological state assessment method that has a subject perform an assignment that comprises multiple tasks and that sets up a rest period, that is a time period during which a task is not given, between a specified task and the following task, and is a method that assesses the psychological state when performing the assignment, wherein time change data when resting is extracted by measuring the intensity of specified parameter signals having a correlation to the amount of blood and/or the amount of blood components of a specified measurement site of the brain of the aforementioned subject, by calculating the amount of blood and/or the amount of blood components based on the parameter signal intensity, and by generating time change data indicating the time changes of the amount of blood and/or the amount of blood components respectively when performing a task and when resting; and the psychological state of the subject when performing the assignment is assessed based on time change data during that rest period.

According to the device of the present invention, it is possible to assess what kind of psychological state the subject was in while performing the assignment by detecting the time changes in the amount of blood and/or the amount of blood components while resting, analyzing the trends observed in those changes over time, and making a comparative study of the amount of blood and/or the amount of blood components of the immediately prior and immediately following states while a task is being performed. Further, by allowing feedback to the time change data of the amount of blood and/or the amount of blood components when performing the assignment obtained for each subject respectively, these psychological state assessment results are useful in accurate analysis of hemodynamics of each subject while performing an assignment.

BRIEF DESCRIPTION OF THE DRAWINGS

FIG. 4 is a diagram indicating the contents of the assignment K1 of the same embodiment;

DETAILED DESCRIPTION OF THE PREFERRED EMBODIMENTS

Psychological state assessment device 1, which is one embodiment of the present invention, will be explained while referring to the diagrams.

Figure 1:
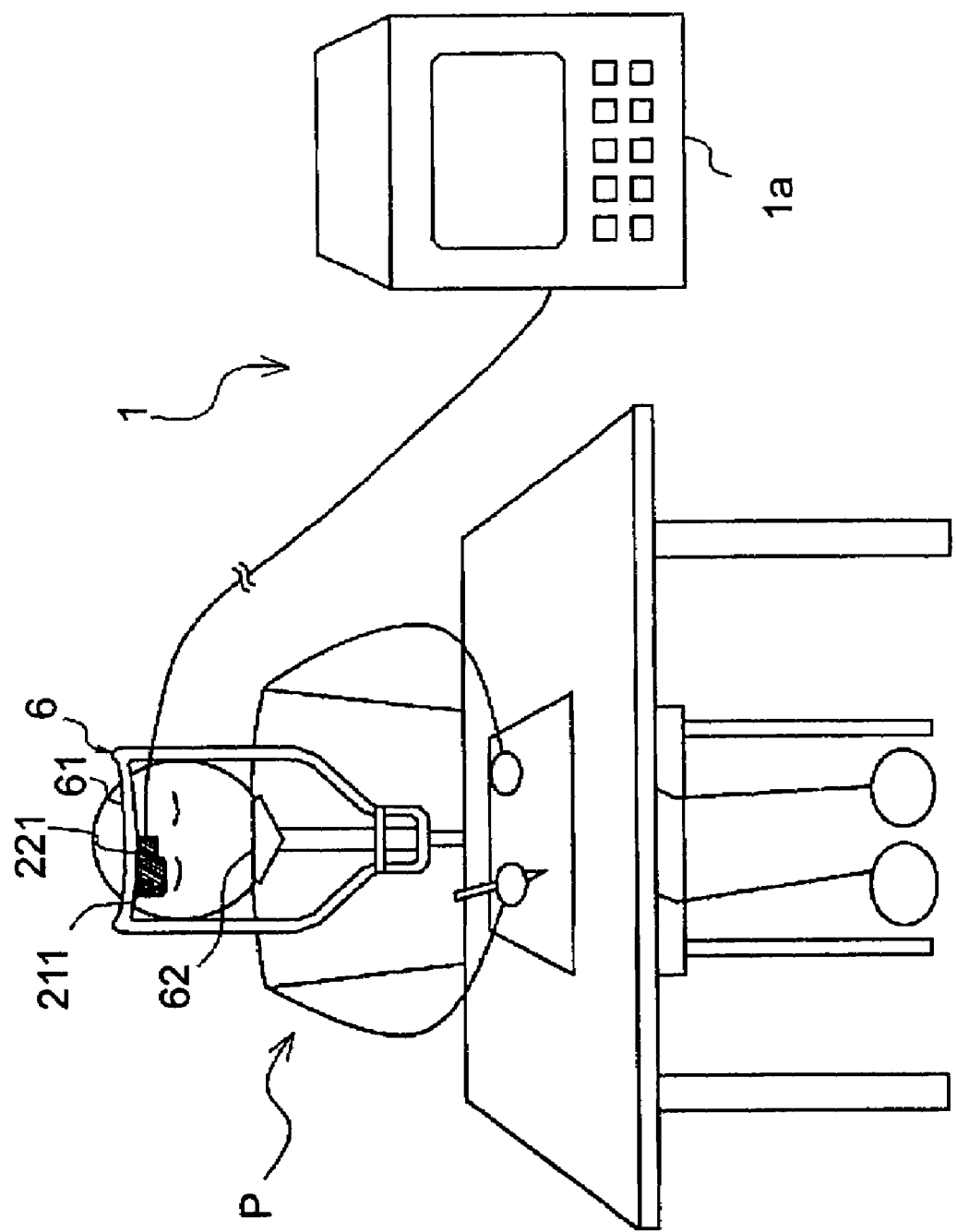
FIG. 1 is an overall schematic diagram indicating the psychological state assessment device of one embodiment of the present invention.
Figure 3:
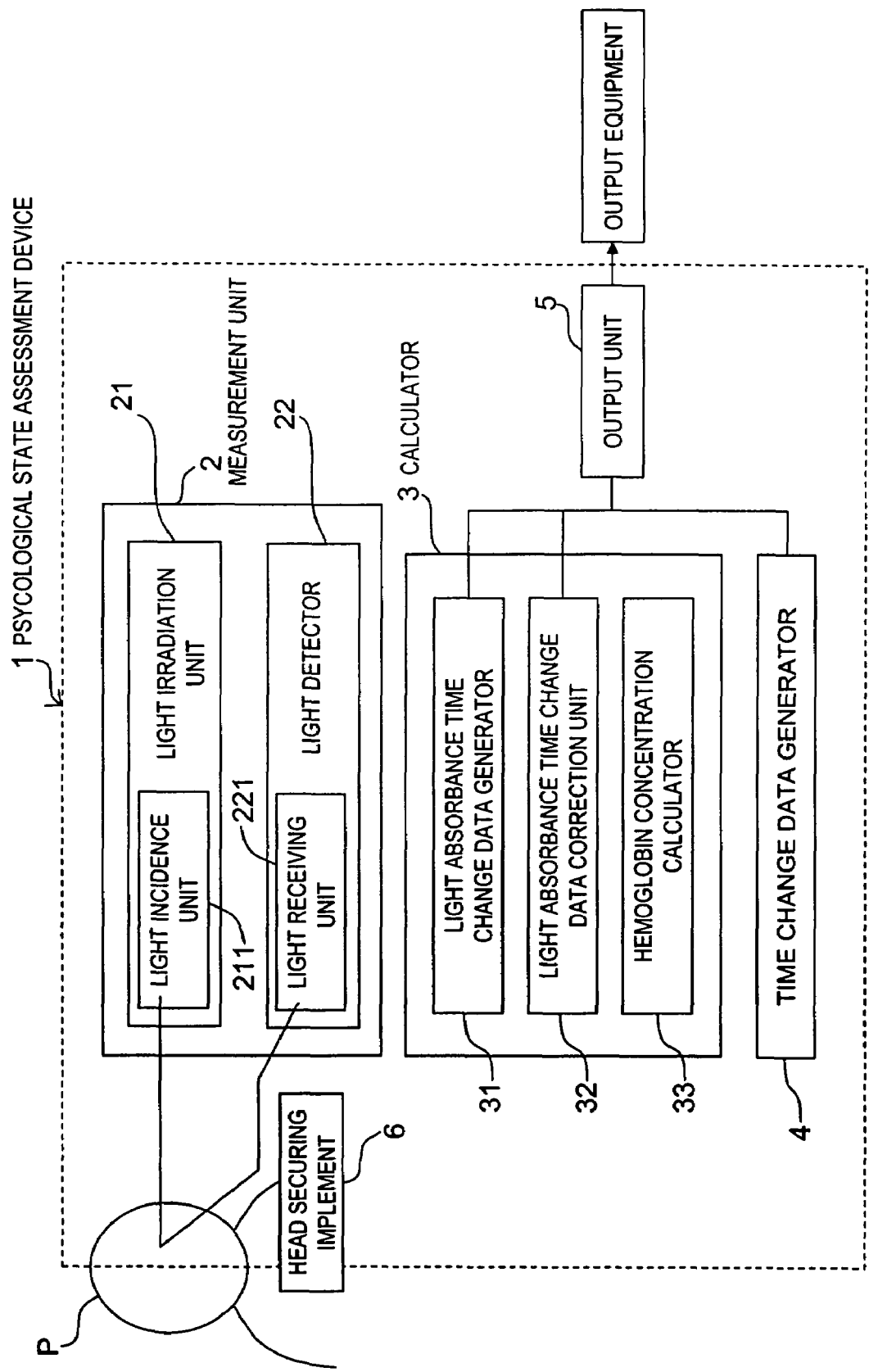
FIG. 3 is an overall functional configurational diagram of the body activity measurement device of the same embodiment.

The psychological state assessment device 1 uses NIRS (near infrared spectroscopy), and is a device for the purpose of having a subject P perform an assignment that comprises multiple tasks and that sets up a rest period, that is a set time during which a task is not given, between a specified task and the following task, and for the purpose of assessing the psychological state while performing the task. As indicated in FIGS. 1 and 3, the device comprises: a measurement unit 2 that irradiates the specified measurement site of the brain of a subject P with near infrared light of a specified wavelength, detects the exiting light which is parameter signals that exit from the aforementioned measurement site based on the irradiated light, and measures the intensity thereof; a calculator 3 that calculates the amount of blood and/or the amount of blood components of the aforementioned measurement site based on the intensity of the exiting light measured by the measurement unit; a time change data generator 4 that acquires in a time sequence the amount of blood and/or the amount of blood components calculated by the calculator 3 and generates hemoglobin concentration time change data which is time change data indicating time changes of the amount of blood and/or the amount of blood components respectively when the subject is performing a task and when resting; an output unit 5 that outputs such that a distinction can be made between the hemoglobin concentration time change data while performing the task and the hemoglobin concentration time change data while at rest, both of which are generated by the time change data generator 4, and also outputs such that the specified hemoglobin concentration time change data while at rest can be compared with the immediately prior and immediately following hemoglobin concentration time change data while performing the task; and a head securing implement 6.

Figure 2:
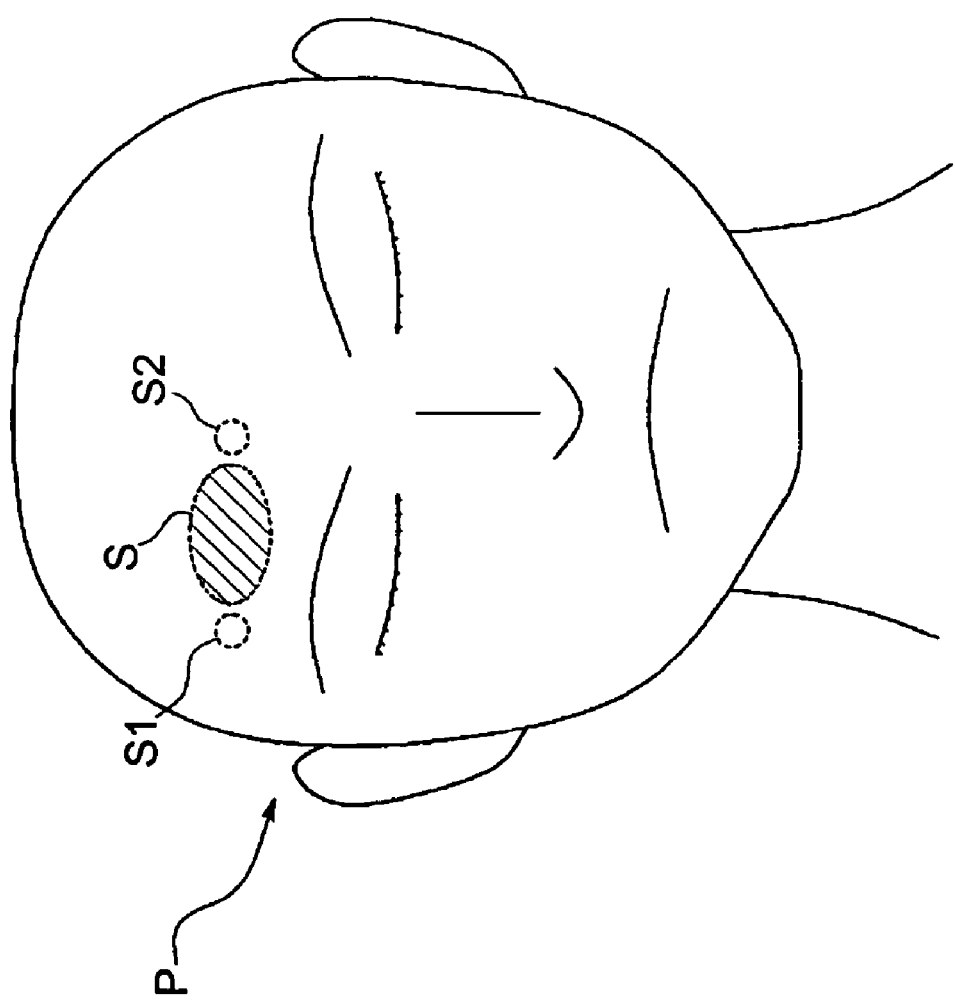
FIG. 2 is a partial explanatory diagram indicating the specified measurement site of the same embodiment.

Describing each unit in more detail, the measurement unit 2 comprises the functions of a light irradiation unit 21 and a light detector 22. The light irradiation unit 21 irradiates a specified site S of the brain (refer to FIG. 2) with near infrared light of multiple wavelengths (3 wavelengths in the present embodiment) emitted from a semiconductor laser light source, etc. In the example indicated in the diagrams, light from the light source provided in device main unit 1a is transmitted by optical fibers, and is irradiated into the brain by light incidence unit 211 (refer to FIG. 1).

Meanwhile, the light detector 22 receives each of the near infrared light, which is the light irradiated by the aforementioned light incidence unit 211 and reflected from the brain, by a light receiving element such as a photo multiplier tube or a CCD element, and converts the intensities thereof to electronic signals. In the example indicated in the diagrams, the light reflected from the brain is focused by the light focus unit 221 (refer to FIG. 1), and the light is transmitted by optical fibers to the light receiving element. Then, as indicated in FIG. 1, when subject P is made to perform an assignment, the aforementioned light incidence unit 211 and the light receiving unit 221 are mounted on the forehead of the subject P.

In the present embodiment, a 1-channel device comprising a pair of the aforementioned light incidence unitr 211 and light receiving unit 221 is adopted. These light incidence unit 211 and light receiving unit 221 are respectively mounted at specified sites S1 and S2 of the forehead of the subject P, and measure the amount of oxyHb (oxygenated hemoglobin) and the amount of deoxyHb (deoxygenated hemoglobin) in the blood at the single specified measurement site S on the brain between these units. Here, the measurement site S is set up, for example, at the frontal lobe of the brain, but to specify to a specific site, a structural image of the brain of the subject P is first obtained using a brain structure measurement device such as an MRI (magnetic Resonance Imaging) which subjects the brain tissue to both electromagnetic radition and a magnetic field to provide a composite image, and then the setup is conducted based on the image.

In the present embodiment, the CPU is made to operate following a specified program and the calculator 3 calculates the baseline corrected amounts of oxyHb, and deoxyHb, that is, the concentrations of oxyHb and deoxyHb, in the blood when performing a task and when resting respectively from the exiting light intensity measured by the aforementioned measurement unit 2 and the exiting light intensity measured when resting. More concretely, the calculator 3 comprises a light absorbance time sequence data generator 31, a light absorbance time change data correction unit 32, and a hemoglobin concentration calculator 33 which is a blood amount and/or blood components amount calculator.

The light absorbance time sequence data generator 31 generates light absorbance time change data (refer to FIG. 6) indicating the time changes of the light absorbance at the various wavelengths by: sampling at specified intervals and acquiring in a time sequence exiting light intensities measured by the aforementioned measurement unit 2; calculating the light absorbance of the respective wavelengths at the aforementioned measurement site by logarithmic conversion and processing based on the exiting light absorbance; relating the light absorbance to the measurement time; and memorizing this data in a specified memory.

Figure 7:
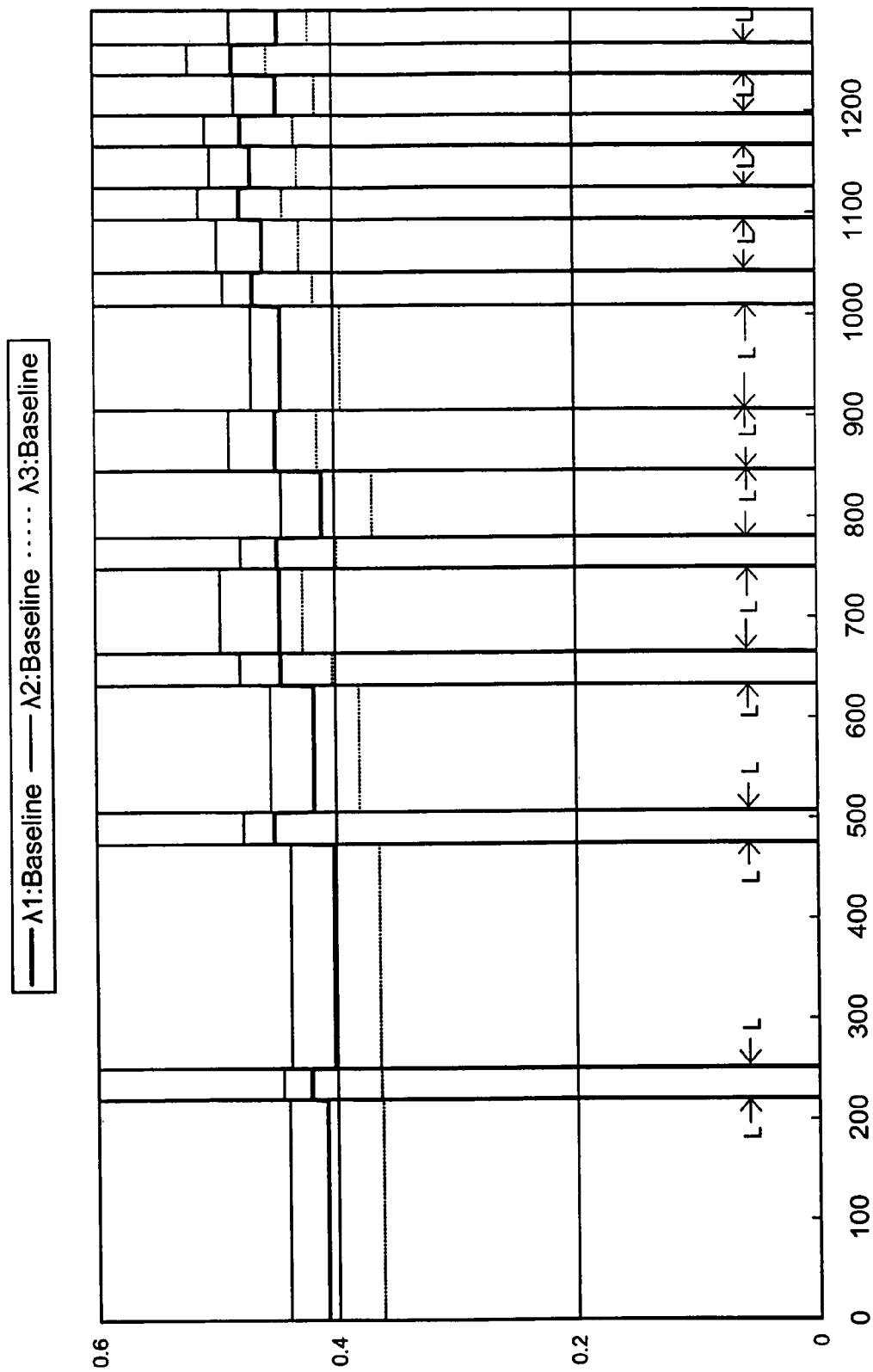
FIG. 7 is a graph indicating the baseline used for the subject P1 of the same embodiment.

The light absorbance time change data correction unit 32 performs baseline corrections of the aforementioned light absorbance time change data while performing a task and while at rest respectively. The present embodiment is set up such that the differential is taken by setting the light intensity at the initial time the task is performed as the baseline for the light absorbance related to when a task is performed, and by setting the light absorbance at the initial time of rest as the baseline for the light absorbance related to being at rest. Specifically, the baseline data indicating these baselines are as shown in FIG. 7. When the aforementioned light absorbance time sequence data generator 31 calculates the light absorbance time change data by substituting the absolute value of the irradiated light intensity and using a constant that is determined by hardware or software processing, the value holds no clear physical meaning, and is nothing more than a logarithmic converted value of a signal value. However, the constant described above is eliminated because the difference of two logarithmic converted values is taken by using a baseline correction to calculate this difference between the calculated value of the light absorbance and the baseline. For this reason, this differential value has the clear physical significance of the attenuation of light in relation to baseline.

Figure 8:
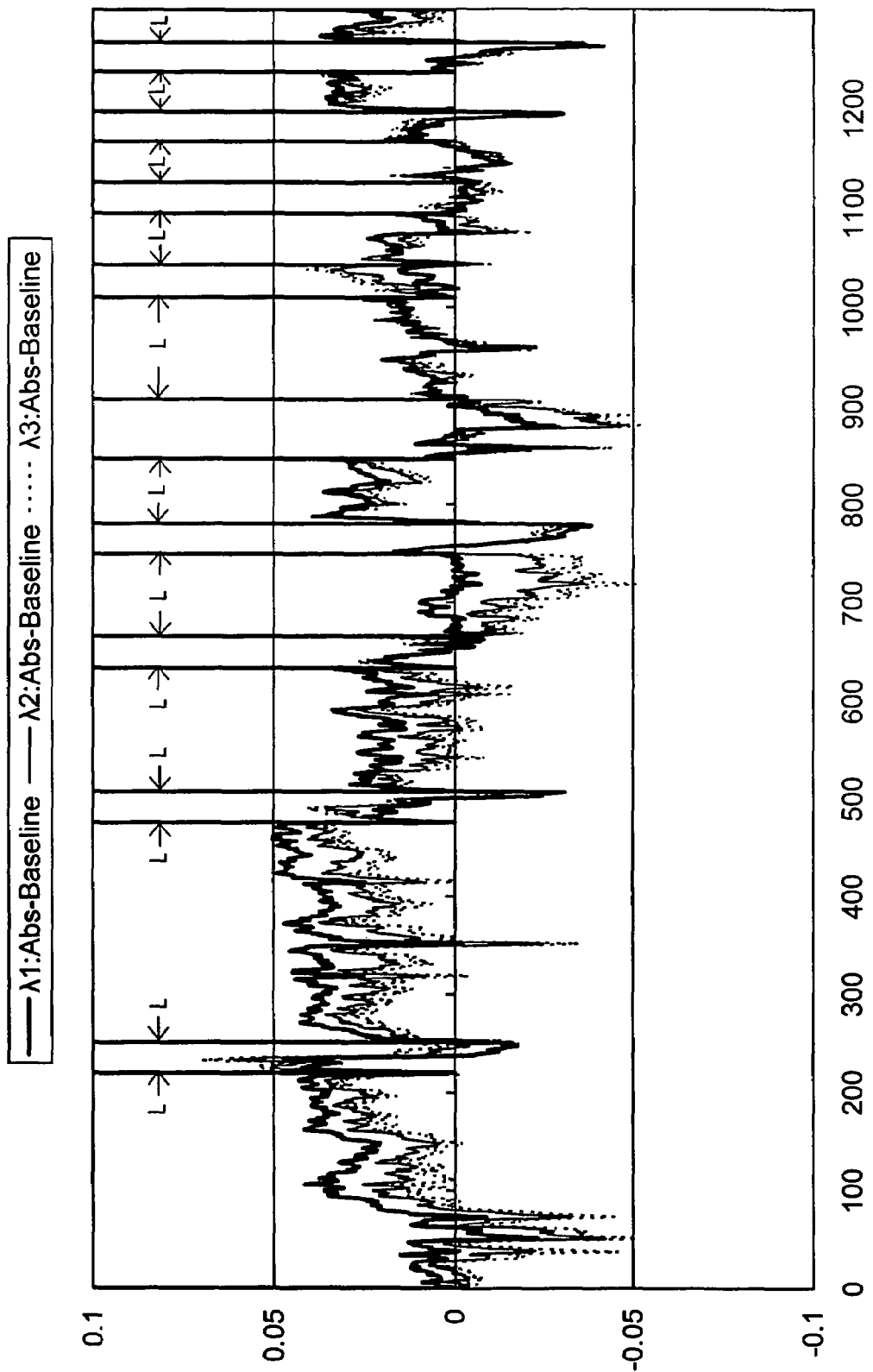
FIG. 8 is a waveform diagram indicating the baseline corrected light absorbance time change data obtained related to the subject P1 of the same embodiment.

The hemoglobin concentration calculator 33 calculates the oxyHb concentration and the deoxyHb concentration equivalent to the amount of oxyHb and the amount of deoxyHb in the blood at the measurement site by using the Modified Lambert-Beer's law to arithmetic process the light absorbance values of the light absorbance time change data that was baseline corrected by the light absorbance time change data correction unit 32 (refer to FIG. 8).

The time change data generator 4 generates hemoglobin concentration time change data, which is data indicating the changes over time for the oxyHb concentration, the deoxyHb concentration, and the total hemoglobin (totalHb) concentration by relating the corresponding sum to the oxyHb and deoxyHb concentrations calculated by the aforementioned hemoglobin concentration calculator 33, and to the totalHb concentration derived from these, and storing these data in a specified memory. In this embodiment the processing is conducted digitally using the CPU, but of course the device may generate hemoglobin concentration sum change data using analog processing.

Figure 6:
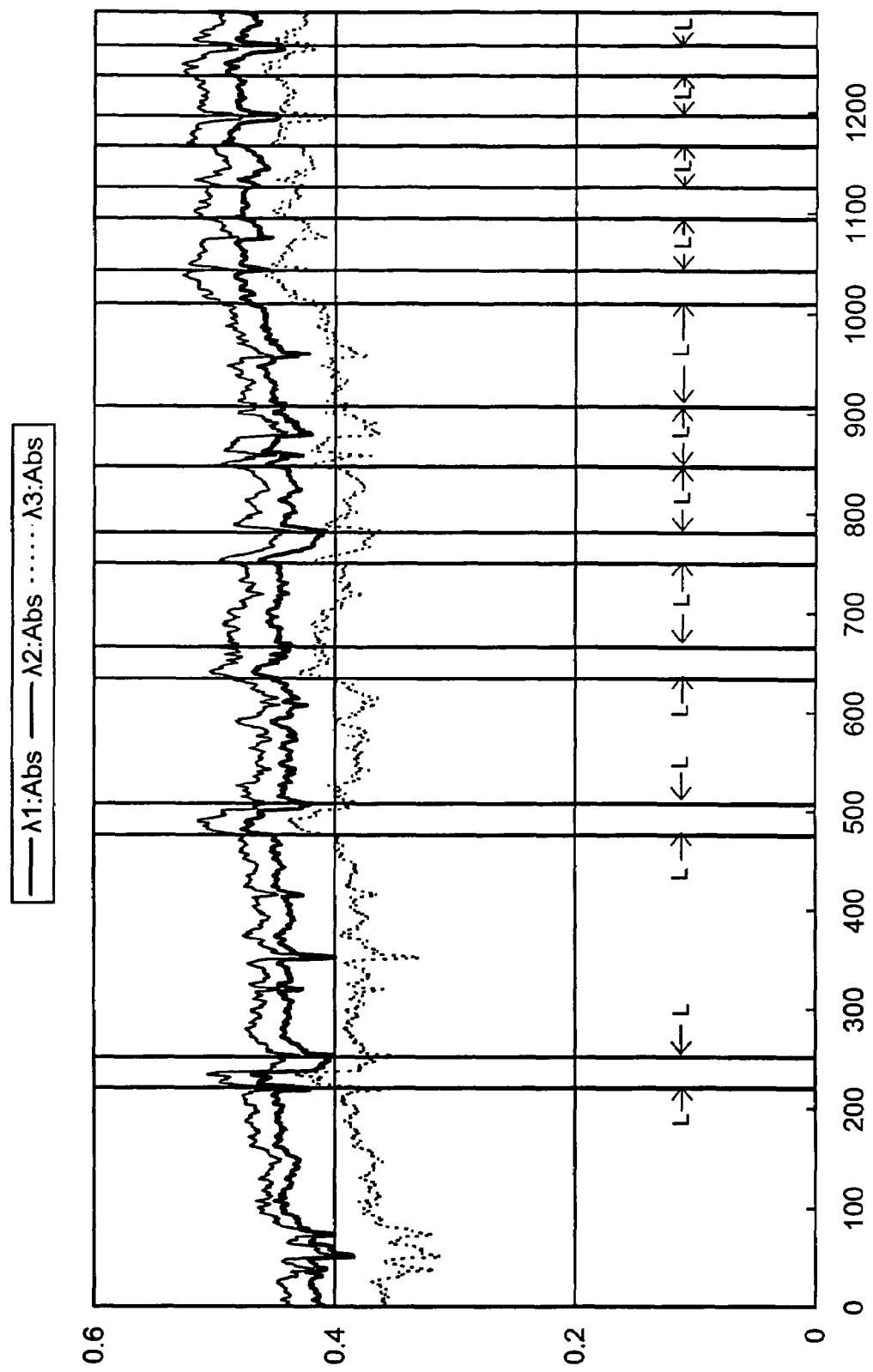
FIG. 6 is a waveform diagram indicating the light absorbance time change data obtained when performing the assignment related to the subject P1 of the same embodiment.

The output unit 5 outputs the waveforms of the aforementioned hemoglobin concentration time change data to an output device such as a display or a printer as indicated in FIGS. 9 to 12. In this embodiment, it is possible to distinguish between when a task is being performed and when the subject is at rest based on a dividing line (indicated by "L" in the diagrams) that shows the timing of the completion of the task (specifically, the beginning of the rest period), and the timing of the completion of the rest period (specifically, the beginning of the performing the task). Further, in this embodiment the timing for the performance of tasks and the completion of the rest periods was measured using photography, for example, based on a video but a means may be provided that automatically recognizes this timing. In addition, because the hemoglobin concentration time change data is output in the form of waveforms in relation to a time axis, it is naturally possible to compare the hemoglobin concentration time changes at a specified time of rest with those of the immediately prior and immediately following times for when a task is performed. Further, the output unit 5 outputs the light absorbance time change data generated by the aforementioned light absorbance time data generator 31 as indicated in FIG. 6, and outputs the baseline data used by the aforementioned light absorbance time change data correction unit 32 and the light absorbance time change data corrected using the baseline data as indicated in FIGS. 7 and 8, in addition to the aforementioned dividing lines respectively.

The head securing implement 6, as indicated for example in FIG. 1, may be configured from a forehead support 61 that supports the upper part of the forehead, a chin support 62 that supports the chin of the subject P, and a securing part not indicated in the diagram for securing in an immobile manner the forehead support 61 and chin support 62 in relation to the desk or floor where the subject P is seated. Movement of the head is suppressed as much as possible by the head securing implement 6 so that accurate data may be obtained.

Described next are the results of using the psychological state assessment device 1 of the present embodiment configured in the manner above to assess the psychological state when subjects P1 and P2 continuously perform assignments K1 and K2, which include multiple tasks and set up rests, time during which a task is not given, between a specified task and the following task.

First, the assignments K1 and K2 will be explained. The task given in the assignment K1 is to solve how many of the given multiple assignment figures Z2 match with the two dimensional designated figure Z1 for which a specified pattern is depicted as in FIG. 4, and to determine whether or not there is the match described above by using a transparent supplement sheet A on which is printed patterns that match with the aforementioned designated figure Z1. Further, it is set up so that parallel, symmetric and rotated patterns also match with the designated figure Z1. The designated figure Z1 indicated in FIG. 4 depicts a pattern that combines multiple lines in a square (for example, 3.2 cm×3.2 cm) arranged in the center of the response sheet. Moreover, the assignment figure Z2 depicts various patterns inside of squares the same size as the designated figure Z1, and 8 of these squares are drawn around the perimeter of the aforementioned designated figure Z1.

Figure 5:
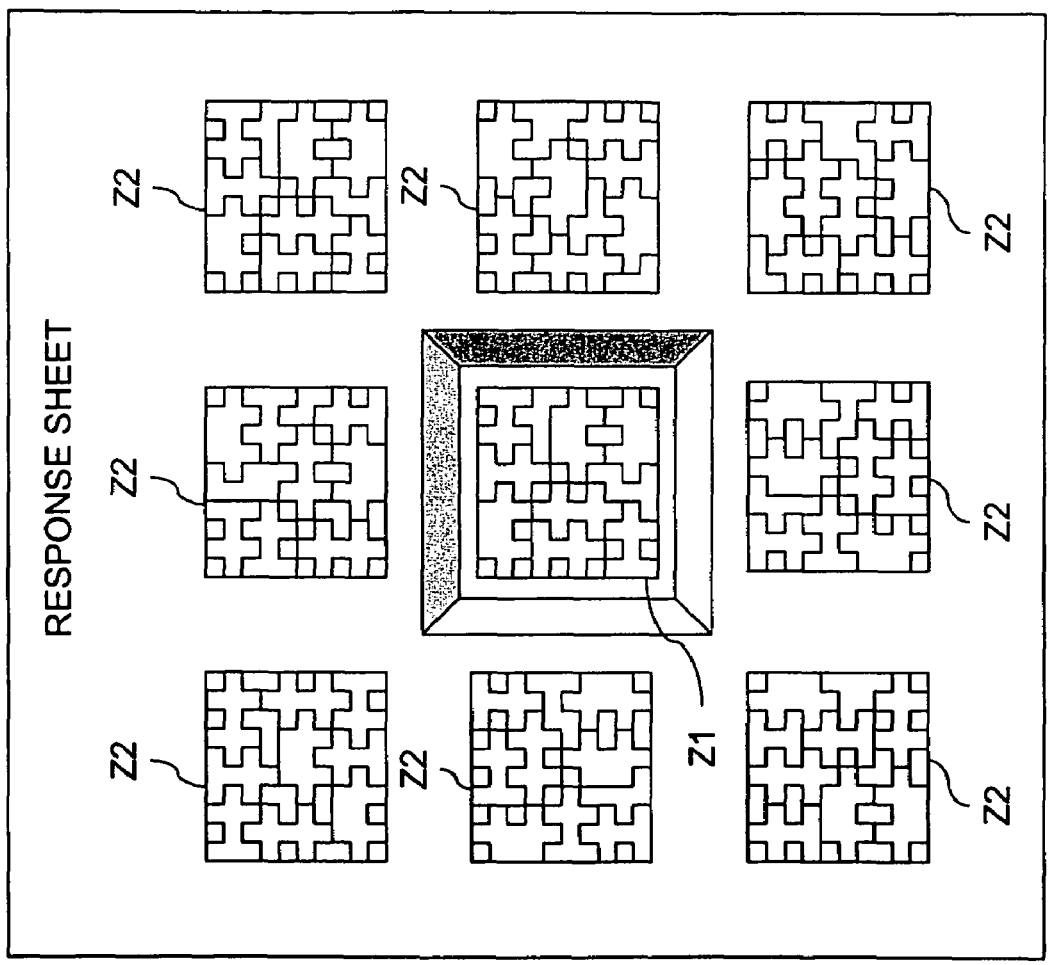
FIG. 5 is a diagram indicating the contents of the assignment K2 of the same embodiment.

Meanwhile, as indicated in FIG. 5, the task given in the assignment K2 is to respond with the number of figures among the multiple assignment figures Z2 that match with the aforementioned designated figure Z1 in the same way as in assignment K1, but the aforementioned supplement sheet A is not provided.

In addition, both assignments K1 and K2 are set up with 30-second rests between the aforementioned specified task and the following task respectively.

Figure 9:
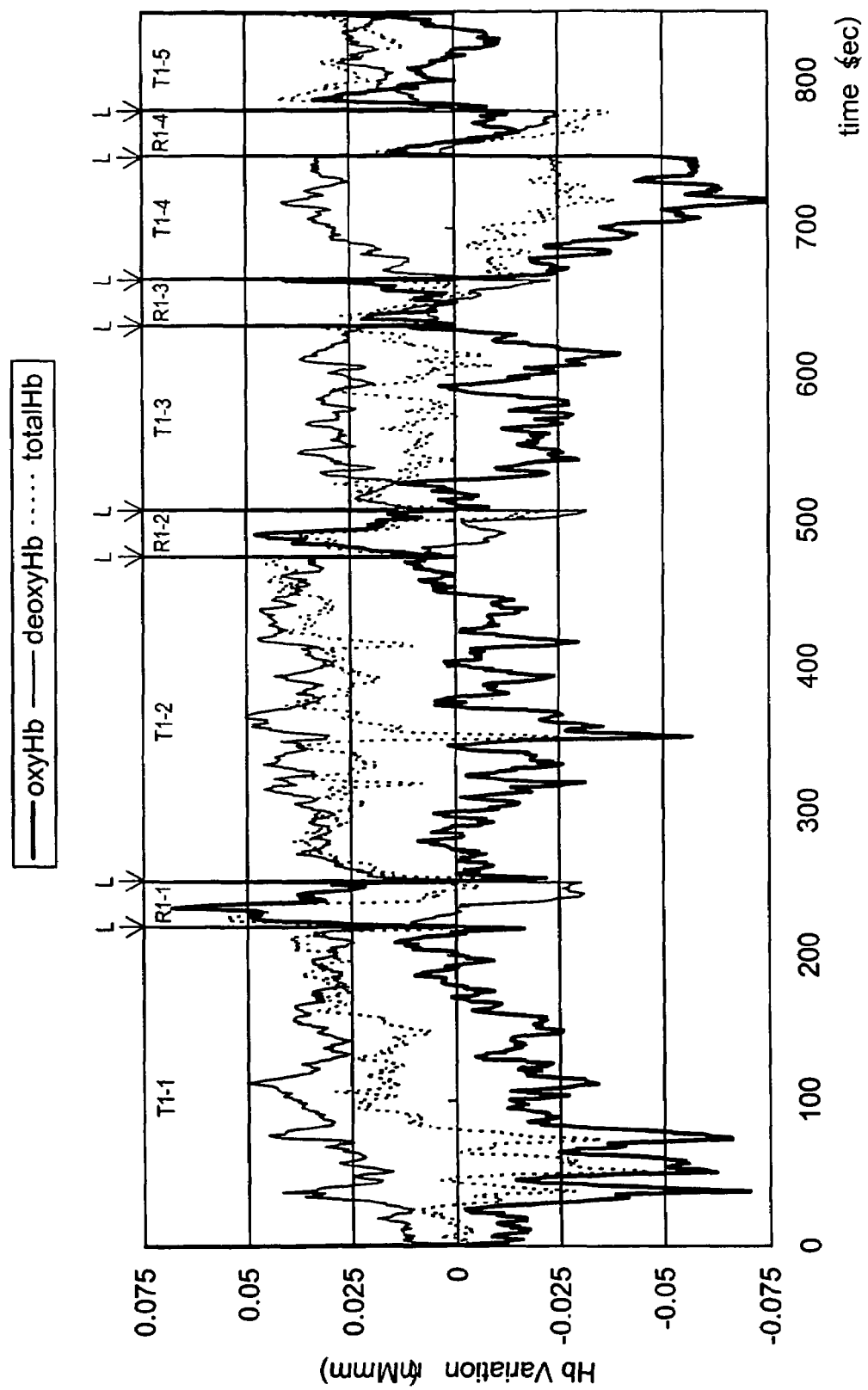
FIG. 9 is a waveform diagram indicating the hemoglobin concentration time sequence data when performing the assignment K1 related to the subject P1 of the same embodiment.
Figure 10:
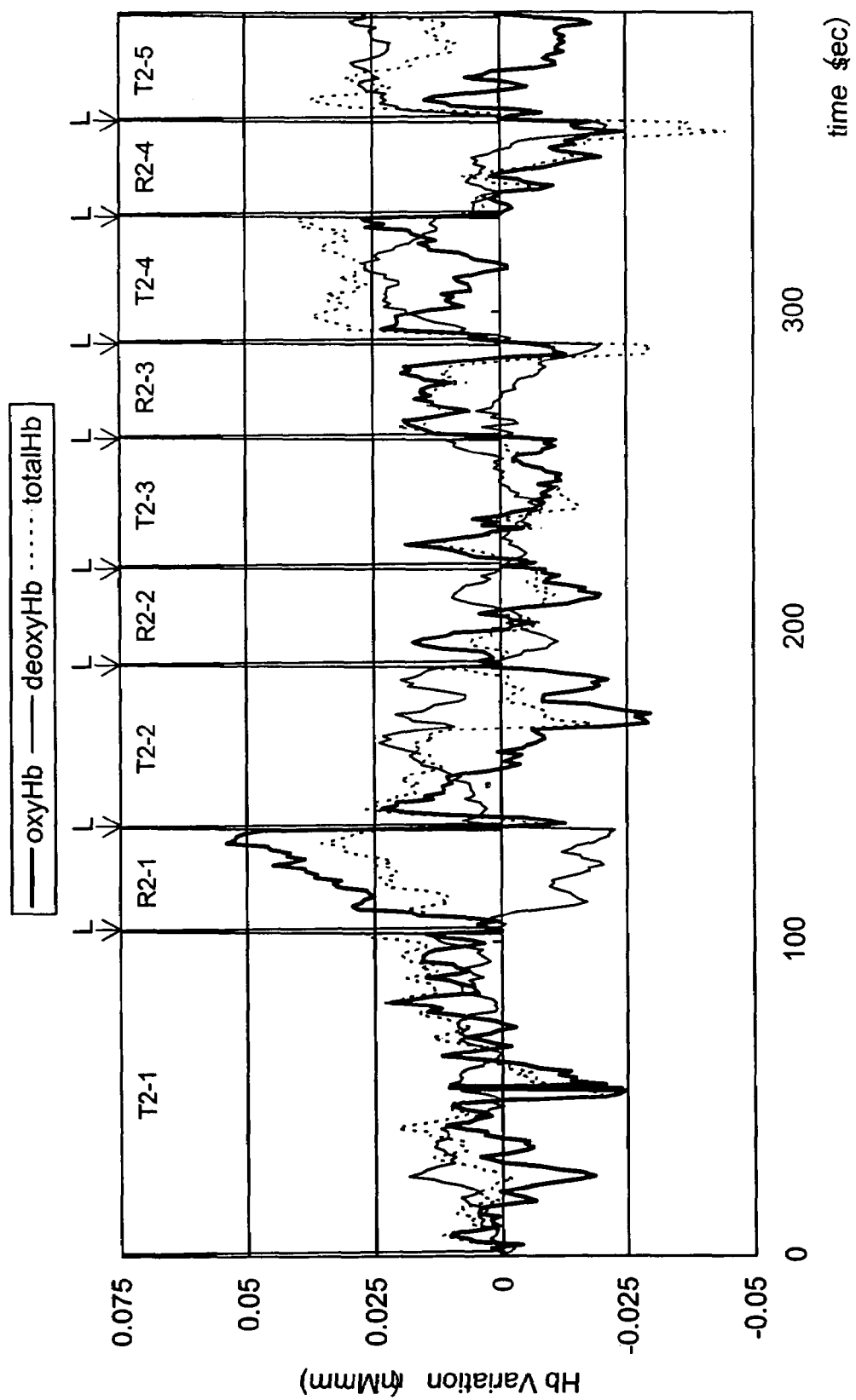
FIG. 10 is a waveform diagram indicating the hemoglobin concentration time sequence data when performing the assignment K2 related to the subject P1 of the same embodiment.
Figure 11:
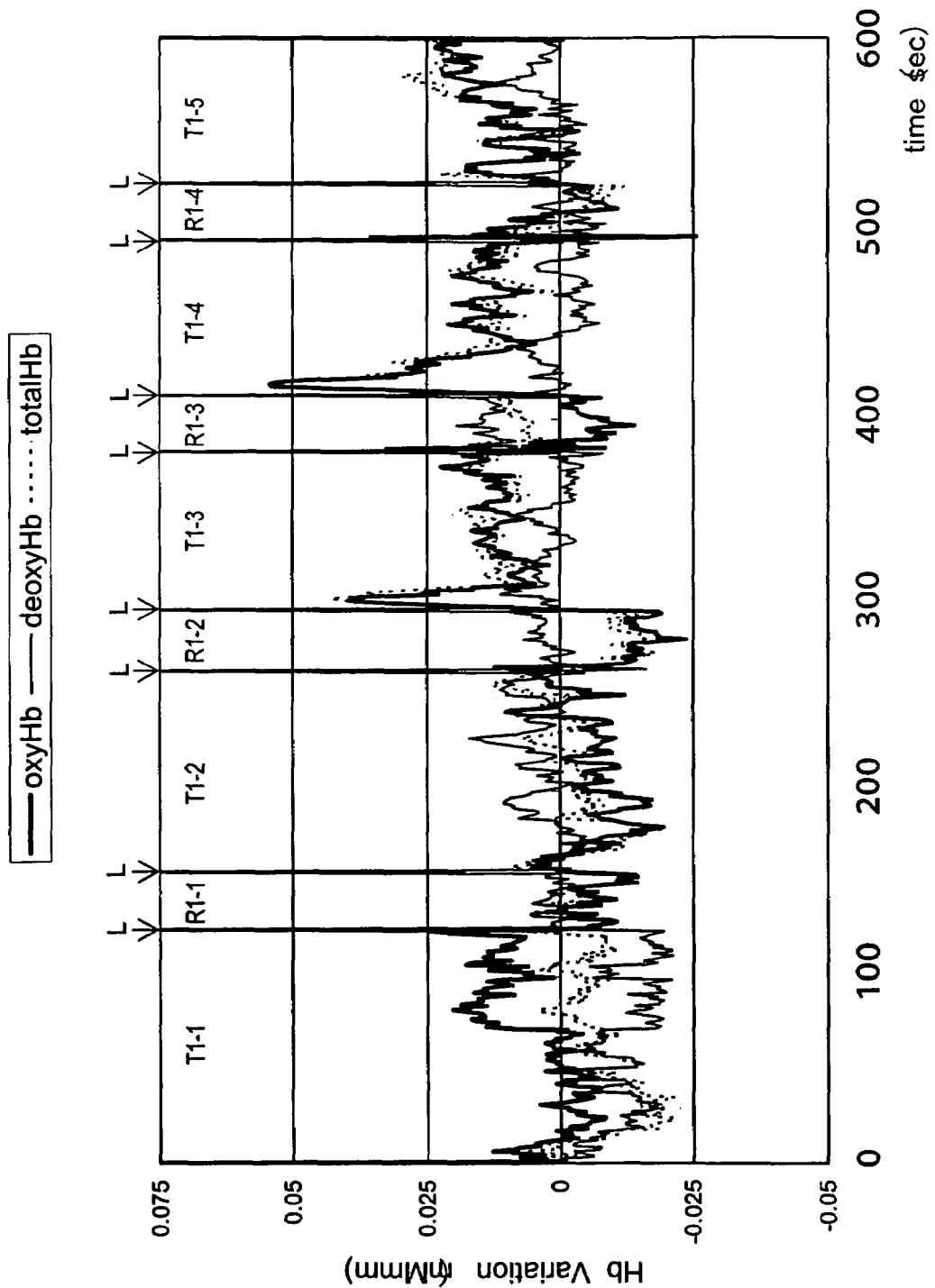
FIG. 11 is a waveform diagram indicating the hemoglobin concentration time sequence data when performing the assignment K1 related to the subject P2 of the same embodiment.
Figure 12:
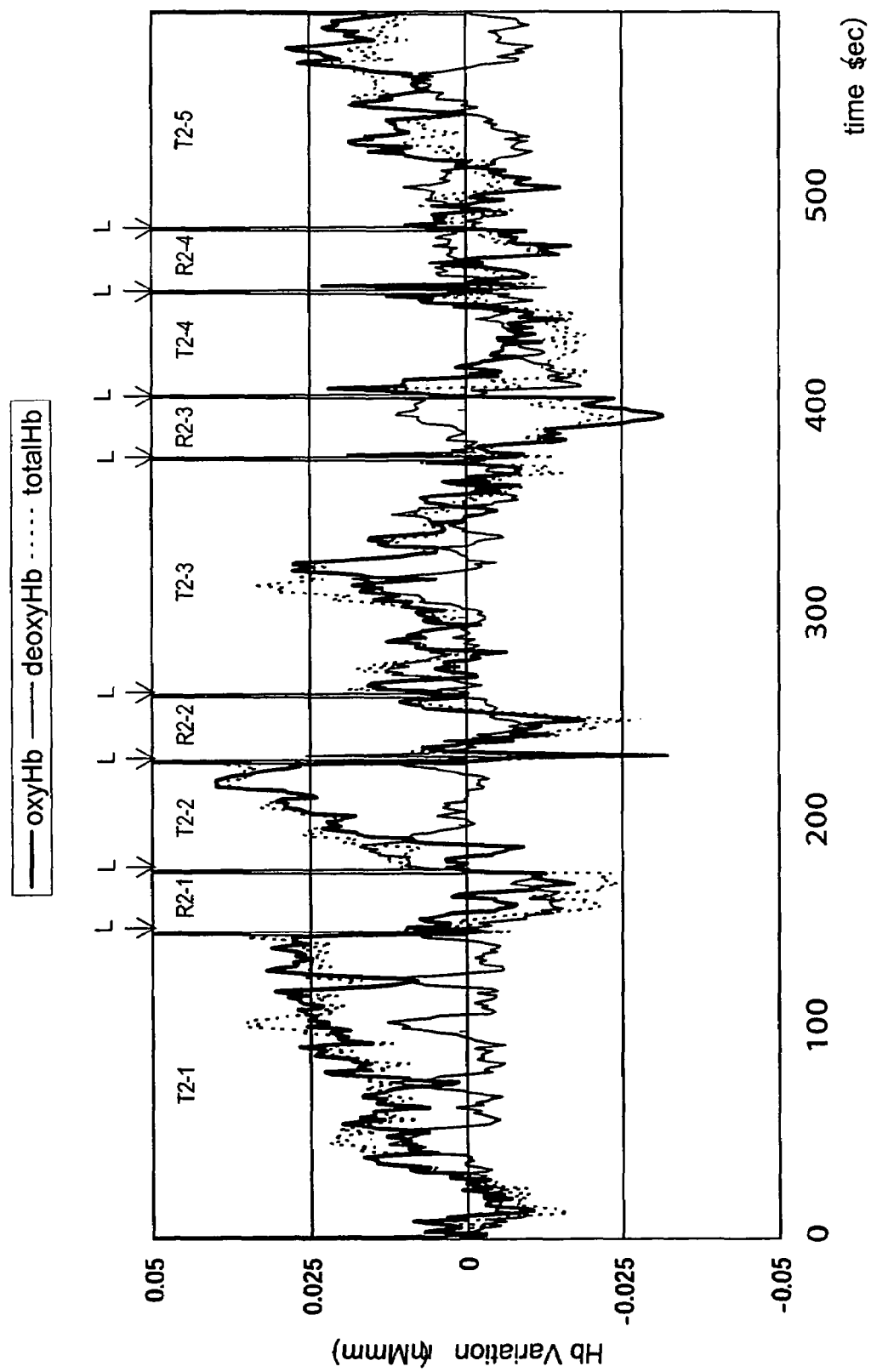
FIG. 12 is a waveform diagram indicating the hemoglobin concentration time sequence data when performing the assignment K2 related to the subject P2 of the same embodiment.

Here, the hemoglobin concentration time change data for the time during which the subjects P1 and P2 perform the assignment K1 are as indicated in FIGS. 9 and 11, and the hemoglobin concentration time change data for the time during which assignment K2 is performed are as indicated in FIGS. 10 and 12. T1-1 to T1-5 in FIGS. 9 and 11 indicate the times when performing the task in assignment K1; and R1-1 to R1-4 indicate the times of rest. Moreover, T2-1 to T2-5 in FIGS. 10 and 12 indicate the times when performing the task of the assignment K2; and R2-1 to R2-4 indicate the times of rest. Further, FIGS. 6 to 8, which have already been explained, are data relating to the subject P1.

According to FIG. 9, at the first to fourth rests, the concentrations of oxyHb suddenly increased from the values when performing the immediately prior task and then decreased, and the width of those increases became smaller as each turn was repeated. In addition, according to FIG. 10, at the times of the first, second and third rests the concentration of oxyHb suddenly increased from the value when performing the immediately prior task and then decreased, and the width of that increase was the largest the first time. That is, the subject P1 had a feeling or "attitude" of tension to the task that had to be implemented immediately thereafter, but it could be assessed that this "attitude" decreased as the task was repeated. This agrees with the impression of subject P1 that "In both assignments K1 and K2, it became easier to find a solution the more times the task was repeated." Further, the oxyHb concentration at the time of rest in assignment K1 indicated higher values overall than the oxyHb concentration at the time of rest in assignment K2, and therefore, it was possible to assess a larger feeling of tension when performing assignment K1 conducted in the first half than when performing assignment K2 conducted in the latter half. This matches the impression of the subject P1 that "Compared to assignment K1 in the first half, I became accustomed to wearing the head securing implement 6 and to the people present in the surroundings, and I was able to be relaxed and concentrate when performing assignment K2 in the latter half."

According to FIGS. 11 and 12, the oxyHb concentrations at the time of rest in both assignments K1 and K2 indicated values greatly reduced (values near 0) from the time of the immediately prior task, and decreased further during rest. Then at the time of the immediately following task, broad increases were again observed. Specifically, it could be assessed that the subject P2 had no particular tension between a specified task and the following task given in assignments K1 and K2. This matches the impression of the subject that "It was easier and quicker to do than I anticipated." Further, in the same way as with the subject P1, the oxyHb concentration at the time of rest in the assignment K1 of the subject P2 also revealed overall greater values than the oxyHb concentrations at the time of rest in the assignment K2, and therefore, it could be assessed that the feeling of tension was greater when performing the assignment K1 conducted in the first half than with the assignment K2 conducted in the latter half. This matches the impression of the subject P2 that "The assignment K2 felt easier than the assignment K1."

As explained in detail above, according to the psychological state assessment device 1 of the present embodiment, it was possible to precisely assess what kind of psychological state the subjects P1 and P2 were in during performance of the assignments by comparing the trends observed in the time changes of the hemoglobin concentrations when resting with the time changes of the hemoglobin concentrations when performing the immediately prior and immediately following tasks.

Moreover, the data is highly reliable because the oxyHb concentration and the deoxyHb concentration were not generally corrected using the value at the time of rest as the baseline as was done in the past, but rather separate baseline corrected values were utilized respectively for the times of performing the tasks and the times of rest.

There was hardly any discomfort for the subjects P when performing the assignment because a compact 1-channel device comprising a pair of the light incidence unit 211 and the light receiving unit 221 was adopted for the measurement unit 2, and it was possible for the mounting of the light incidence unit 211 and the light receiving unit 221 to have no effect on the assessment of the psychological state.

In addition, time changes of the oxyHb concentration, deoxyHb concentration and totalHb concentration when performing the assignment were immediately and precisely understood because the output unit 5 is made to output waveforms of the hemoglobin concentration time change data when performing the task and when resting. Furthermore, the construction is simple.

The present invention is not limited to the embodiment above.

For example, the form of outputting the time change data by the output unit is not limited to waveforms, and bar graphs or numeric values may be output. Moreover, as long as the time change data when performing the task can be distinguished from the time change data when resting, the device is not limited to arranging a dividing line as in the embodiment above, and, for example, a variety of forms are possible such as making the distinction by using another graphic, for example, an arrow, or by using color differences such as the color of the waveforms indicating the data or the background color.

Moreover, the device may comprise an information storage unit that in advance stores multiple pattern data for time change data when resting and time change data when performing the immediately prior and immediately following tasks in relation to the corresponding psychological state characteristics data, and an assessment unit that refers to the aforementioned pattern data to analyze and automatically assess the time change data generated by the time change data generator.

The multiple tasks comprised in the assignment are not limited to those described above, and may be tasks such as exercise, and a stimulus to the five senses, for example, "having the subject listen to something", "having the subject look at something".

The specified parameter signals having a correlative relation to the amount of blood and/or the amount of blood components may include the intensity of luminescent light obtained when irradiating the brain with light of a specified wavelength, or the intensity of electromagnetic waves outside the visible spectrum such as the size of the changes of magnetic fields, and radioactive rays.

Those skilled in the art will appreciate that various adaptations and modifications of the just-described preferred embodiment can be configured without departing from the scope and spirit of the invention. Therefore, it is to be understood that, within the scope of the amended claims, the invention may be practiced other than as specifically described herein.

The invention claimed is:

1. A psychological state assessment device which has a subject perform an assignment that comprises multiple tasks and that sets up a rest, a time during which a task is not given, between a specified task and the following task, and which assesses the psychological state when performing the assignment, comprising:
   a measurement unit that detects specified parameter signals having a correlation to the amount of blood and/or the amount of blood components in a specified measurement site in the brain of the aforementioned subject, and measures the intensity of the parameter signals;
   a calculator that calculates the amount of blood and/or amount of blood components based on the parameter signal intensities that the measurement unit measures;

a time change data generator that generates time change data indicating the time changes for the amount of blood and/or the amount of blood components when performing a task and when resting respectively by acquiring sequentially over time the amount of blood and/or the amount of blood components that the calculator calculates; and an output unit that outputs such that a distinction can be made between time change data while performing a task and time change data while at rest, both of which are generated by the time sequence data generator, and also outputs such that the time change data during a specified rest can be compared with time change data while performing the immediately prior and immediately following tasks; and configured such that the psychological state of the subject when performing the assignment is assessed based on the aforementioned time change data while at rest, wherein the aforementioned calculator calculates a baseline corrected amount of blood and/or amount of blood components when performing a task and when resting respectively, based on the parameter signal intensities measured by the aforementioned measurement unit during performance of the task and the parameter signal intensities measured when resting.

2. The psychological state assessment device according to claim 1 wherein the aforementioned measurement unit is configured to irradiate a specified measurement site of the brain with near infrared light of a specified wavelength and is configured to measure the intensity of the exiting light, that is the aforementioned parameter signals, that exits from the aforementioned measurement site based on the irradiated light; and the aforementioned calculator calculates the amount of blood and/or the amount of blood components based on the intensity of the aforementioned exiting light.

3. The psychological state assessment device according to claim 2 wherein the aforementioned measurement unit is a 1-channel device.

4. The psychological state assessment device according to claim 1 wherein the aforementioned measurement unit is configured to irradiate irradiates a specified measurement site of the brain of the subject with near infrared light of a specified wavelength, and is configured to measure the intensity of the exiting light, that is the aforementioned parameter signals, that exits from the aforementioned measurement site based on the intensity of the aforementioned exiting light; and the aforementioned calculator comprises:

a light absorbance time sequence data generator that calculates the light absorbance of a measurement site at a specified wavelength from the intensity of the exiting light measured by the measurement unit, and generates light absorbance time change data indicating the time changes of the light absorbance; a light absorbance time change data correction unit that conducts baseline correction of the light absorbance time change data that the light absorbance time sequence data generator generates respectively while performing a task and while at rest; and a blood amount and/or a blood components amount calculator that calculates the amount of blood and/or the amount of blood components from the light absorbance time change data corrected by the light absorbance time change data correction unit; and light absorbance time sequence data generator; and calculates the baseline corrected amount of blood and/or amount of blood components.

5. The psychological state assessment device according to claim 4 wherein the aforementioned measurement unit is a 1-channel device.

6. The psychological state assessment device according to claim 1 wherein the aforementioned calculator calculates the amount of oxyHb and amount of deoxyfib, as the amount of the blood and/or amount of the blood components, in the blood at the aforementioned measurement site.

7. The psychological state assessment device according to claim 1 wherein the aforementioned output unit outputs the waveforms of the time change data while performing a task and while at rest.

8. A psychological state assessment device which has a subject perform an assignment that comprises multiple tasks and that sets up a rest, a time during which a task is not given, between a specified task and the following task, and which assesses the psychological state when performing the assignment, comprising:

a measurement unit that detects specified parameter signals having a correlation to the amount of blood and/or the amount of blood components in a specified measurement site in the brain of the aforementioned subject, and measures the intensity of the parameter signals;

a calculator that calculates the amount of blood and/or amount of blood components based on the parameter signal intensities that the measurement unit measures;

a time change data generator that generates time change data indicating the time changes for the amount of blood and/or the amount of blood components when performing a task and when resting respectively by acquiring sequentially over time the amount of blood and/or the amount of blood components that the calculator calculates; and an output unit that outputs such that a distinction can be made between time change data while performing a task and time change data while at rest, both of which are generated by the time sequence data generator, and also outputs such that the time change data during a specified rest can be compared with time change data while performing the immediately prior and immediately following tasks; and configured such that the psychological state of the subject when performing the assignment is assessed based on the aforementioned time change data while at rest, wherein a calculator calculates the aforementioned baseline corrected amount of blood and/or amount of blood components as the amount of blood and/or the amount of blood components in which baselines are subtracted from the value of the amount of blood and/or the amount of blood components calculated by specified computations based on the parameter signal intensities; and in relation to the calculated values of the amount of blood and/or the amount of blood components when performing a task, the value of the amount of blood and/or the amount of blood components at the initial time the task is performed is taken to be the baseline, and in relation to the calculated values of the amount of blood and/or the amount of blood components while resting, the value of the amount of blood and/or the amount of blood components at the initial point of rest is taken to be the baseline.

9. The psychological state assessment device according to claim 8 wherein the aforementioned measurement unit is configured to irradiate a specified measurement site of the brain with near infrared light of a specified wavelength and is configured to measure the intensity of the exiting light, that is the aforementioned parameter signals, that exits from the aforementioned measurement site based on the irradiated light; and the aforementioned calculator calculates. the amount of blood and/or the amount of blood components based on the intensity of the aforementioned exiting light.

10. The psychological state assessment device according to claim 8 wherein the aforementioned measurement unit is configured to irradiate a specified measurement site of the brain of the subject with near infrared light of a specified wavelength, and is configured to measure the intensity of the exiting light, that is the aforementioned parameter signals, that exits from the aforementioned measurement site based on the intensity of the aforementioned exiting light; and the aforementioned calculator comprises:

a light absorbance time sequence data generator that calculates the light absorbance of a measurement site at a specified wavelength from the intensity of the exiting light measured by the measurement unit, and generates light absorbance time change data indicating the time changes of the light absorbance; a light absorbance time change data correction unit that conducts baseline correction of the light absorbance time change data that the light absorbance time sequence data generator generates respectively while performing a task and while at rest; and a blood amount and/or a blood components amount calculator that calculates the amount of blood and/or the amount of blood components from the light absorbance time change data corrected by the light absorbance time change data correction unit; and light absorbance time sequence data generator; and calculates the baseline corrected amount of blood and/or amount of blood components.

11. The psychological state assessment device according to claim 8 wherein the aforementioned calculator calculates the amount of oxyHb and amount of deoxyHb, as the amount of the blood and/or the amount of the blood components, in the blood at the aforementioned measurement site.

12. The psychological state assessment device according to claim 8 wherein the aforementioned output unit outputs the wave forms of the time change data while performing a task and while at rest.

13. A psychological state assessment method that has a subject perform an assignment that comprises multiple tasks and that sets up a rest, a time during which a task is not given, between a specified task and the following task, and assesses the psychological state while performing the assignment, wherein time change data when resting is extracted by measuring the intensity of specified parameter signals having a correlation to the amount of blood and/or the amount of blood components of a specified measurement site of the brain of the aforementioned subject, by calculating the amount of blood and/or the amount of blood components based on the parameter signal intensity, and by generating time change data indicating the time changes in the amount of blood and/or the amount of blood components while performing a task and while at rest respectively; and the psychological state of the subject when performing the assignment is assessed by analyzing the time change data when resting.

14. A method of measuring brain activity during predetermined assigned tasks to be performed by a subject, comprising:

applying electromagnetic radiation and a magnetic field to provide a composite image of a brain;

selecting a measurement site appropriate to measure oxyHb and deoxyHb from the composite image;

applying sensors to the measurement site of the subject to enable measurement of the amount of oxyHb and deoxyHb;

having the subject perform a test cycle of predetermined assigned tasks with a predetermined rest period provided between the tasks;

measuring the oxyHb and deoxyHb during the assigned tasks and the rest period of the test cycle;

calculating changes in the oxyHb and deoxyHb during the test cycle;

calculating a baseline correction value from the changes in oxyHb and deoxyHb based on the relative changes in value from the rest period and the assigned tasks; and applying the baseline correction value to the measured oxyHb and deoxyHb to determine a psychological state of the subject.

15. A psychological state assessment method that has a subject perform an assignment that comprises multiple tasks and that sets up a rest, a time during which a task is not given, between a specified task and the following task, and assesses the psychological state while performing the assignment, wherein time change data when resting is extracted by measuring the intensity of specified parameter signals having a correlation to the amount of blood and/or the amount of blood components of a specified measurement site of the brain of the aforementioned subject, by calculating a baseline corrected amount of blood and/or amount of blood components when performing a task and when resting respectively, based on the parameter signal intensity during performance of the task and the parameter signal intensity measured when resting, and by generating time change data indicating the time changes in the amount of blood and/or the amount of blood components while performing a task and while at rest respectively; and the psychological state of the subject when performing the assignment is assessed by analyzing the time change data when resting.

16. A psychological state assessment method that has a subject perform an assignment that comprises multiple tasks and that sets up a rest, a time during which a task is not given, between a specified task and the following task, and assesses the psychological state while performing the assignment, wherein time change data when resting is extracted by measuring the intensity of specified parameter signals having a correlation to the amount of blood and/or the amount of blood components of a specified measurement site of the brain of the aforementioned subject, by calculating a baseline corrected amount of blood and/or amount of blood components when performing a task and when resting respectively, based on the parameter signal intensity during performance of the task and the parameter signal intensity measured when resting, and by generating time change data indicating the time changes in the amount of blood and/or the amount of blood components while performing a task and while at rest respectively;

the psychological state of the subject when performing the assignment is assessed by analyzing the time change data when resting, and wherein the baseline corrected amount of blood and/or amount of blood components as the amount of blood and/or the amount of blood components in which baselines are subtracted from the value of the amount of blood and/or the amount of blood components calculated by specified computations based on the parameter signal intensities; and in relation to the calculated values of the amount of blood and/or the amount of blood components when performing a task, the value of the amount of blood and/or the amount of blood components at the initial time the task is performed is taken to be the baseline, and in relation to the calculated values of the amount of blood and/or the amount of blood components while resting, the value of the amount of blood and/or the amount of blood components at the initial point of rest is taken to be the baseline.

* * * * *